United States Patent [19]

Shimura et al.

[11] Patent Number: 5,441,488
[45] Date of Patent: Aug. 15, 1995

[54] MEDICAL TOOL HAVING LUBRICIOUS SURFACE IN A WETTED STATE AND METHOD FOR PRODUCTION THEREOF

[75] Inventors: Kenichi Shimura; Naoki Ishii; Makoto Onishi, all of Kanagawa, Japan

[73] Assignee: Terumo Kabushiki Kaisha, Tokyo, Japan

[21] Appl. No.: 192,574

[22] Filed: Feb. 7, 1994

[30] Foreign Application Priority Data

Feb. 8, 1993 [JP] Japan .................. 5-020171

[51] Int. Cl.$^6$ ............................................. A61M 5/32
[52] U.S. Cl. ........................... 604/265; 424/425
[58] Field of Search ............... 604/265; 427/2, 407, 427/400, 333; 424/425

[56] References Cited

U.S. PATENT DOCUMENTS

| | | | |
|---|---|---|---|
| 4,100,309 | 7/1978 | Micklus et al. | 427/2 |
| 4,666,437 | 5/1987 | Lambert | 604/265 |
| 5,091,205 | 2/1992 | Fan | 604/265 |
| 5,160,790 | 11/1992 | Elton | 604/265 |
| 5,266,359 | 11/1993 | Spielvogel | 604/265 |

FOREIGN PATENT DOCUMENTS

| | | |
|---|---|---|
| 0106004 | 4/1984 | European Pat. Off. . |
| 0166998 | 1/1986 | European Pat. Off. . |
| 0389632A1 | 10/1990 | European Pat. Off. . |
| 0439908A1 | 8/1991 | European Pat. Off. . |
| 0480809A2 | 4/1992 | European Pat. Off. . |
| 59-81341 | 5/1984 | Japan . |
| 1-55023 | 11/1989 | Japan . |
| 4-202441 | 7/1992 | Japan . |
| WO92/19289 | 11/1992 | WIPO . |

*Primary Examiner*—C. Fred Rosenbaum
*Assistant Examiner*—Chalin Smith
*Attorney, Agent, or Firm*—Burns, Doane, Swecker & Mathis

[57] ABSTRACT

This invention provides a medical tool the surface of which is enabled to acquire lasting lubricity (low friction) by assuming a state wetted with bodily fluid or aqueous solution. This surface is formed without requiring the coating work to be repeated. The medical tool is produced by coating a water-swellable polymer having in the molecular unit thereof a reactive functional group capable of being reacted with a proton-donating group, on the surface of a matric material possessing the proton-donating group, and also by coating a water-swellable polymer having in the molecular unit thereof a reactive group capable of being reacted with an acid anhydride group on the surface of a matric material possessing the acid anhydride group.

18 Claims, 1 Drawing Sheet

MEDICAL TOOL HAVING LUBRICIOUS SURFACE IN A WETTED STATE AND METHOD FOR PRODUCTION THEREOF

BACKGROUND OF THE INVENTION

1. Field of the Invention

This invention relates to a medical tool and a method for the production thereof. More particularly, it relates to a medical tool which, owing to a polymer deposited on the surface thereof, manifests excellent lubricity on being wetted and a method for the production of the medical tool.

1. Description of the Prior Art

Generally, for the manufacture of catheters and other similar medical tools, substances of low friction are adopted as matric materials thereof and further such matric materials are coated with a hydrophilic polymer for the sake of precluding the medical tools from inflicting damage on the inner wall surfaces of blood vessels or on the tissues and enhancing the operability of the medical tools. For example, fluorine resin, polyethylene resin, etc. are used as substances of low friction for matric materials and these matric materials are coated with fluorine resin, silicone oil, olive oil, glycerol, etc.

These measures, however, cannot be expected to impart lasting lubricity to the medical tools. The medical tools which embody these measures have a problem of poor safety in the sense that the lubricious substances are liable to exfoliate, peel, or melt from the surfaces of matric materials.

U.S. Pat. No. 4,100,309 makes a disclosure to the effect that a copolymer of polyvinyl pyrrolidone with polyurethane is used as a substance possessed of lubricity. The method taught by this US patent publication is satisfactory in terms of lubricity and lastingness of this quality. Since this method requires at least two kinds of polymer for coating and essentially necessitates the presence of an isocyanate group as a reactive group on the surface of the matric material, the reaction is not obtainable with either a matric material allowing no easy introduction of the isocyanate group or a polymer possessed of lubricity.

JP-A-59-81,341 also discloses a method for impartation of lubricity similarly by utilizing an isocyanate group on the surface of a matric material.

Further, JP-B-1-55,023 discloses a method for binding a copolymer of polyether, polyamide, or polysiloxane through the medium of polyisocyanate to the surface of a matric material of a medical tool. For this method, the interposition of the isocyanate is an essential requirement and the presence on the surface of the matric material of at least one group selected from among amino group, imino group, carboxyl group, and mercapto group is an indispensable requirement. This method, therefore, is incapable of effecting this binding treatment on a medical tool which is made of polyolefin or halogenated polyolefin and has none of the functional groups mentioned above.

The various methods of surface lubrication mentioned above, however, are not desirable from the standpoint of operability because they require the coating operation to be performed at least twice (as for the coating with a cross-linking compound such as isocyanate and the coating with a lubricious substance) when lasting lubricity must be imparted.

Generally, since a low molecular cross-linking agent (such as, for example, a diisocyanate compound or a diepoxy compound which has a highly active functional groups) is possessed of unduly high reactivity, remains as unreacted monomer which is easy to elute and has toxity, the use of such a substance is not desirable even from the standpoint of safety.

As described above, the impartation of lubricity to the surface of a medical tool imposes a limit on the kind of matric material or requires the coating operation to be carried out twice or more where lasting lubricity is necessary.

An object of this invention, therefore, is to provide a novel medical tool and a method for the production thereof.

Another object of this invention is to provide a medical tool the surface of which acquires lasting lubricity (low friction) on being wetted with body fluid or aqueous solvent, obviates the necessity of carrying out the coating operation twice or more for its own formation, and enjoys high safety and a method for the production of the medical tool.

SUMMARY OF THE INVENTION

The objects described above are accomplished by a medical tool which comprises a water-swellable polymer containing a reactive functional group in the molecular unit thereof and a matric material capable of reacting with the reactive functional group and manifests lubricity on being wetted.

This invention discloses a medical tool wherein the matric material contains a proton-donating group which is capable of reacting with the reactive functional group. The invention also discloses a medical tool wherein the reactive functional group is at least one group selected from the class consisting of epoxy group, acid halide group, and isocyanate group. This invention further discloses a medical tool wherein the proton-donating group is at least one group selected from the class consisting of amino group, imino group, hydroxyl group, carboxyl group, and mercapto group. Further, this invention discloses a medical tool wherein the matric material is a material having as one component thereof a synthetic polymeric compound containing an acid anhydride group in the molecular unit thereof and the reactive functional group is capable of reacting the acid anhydride group.

The objects described above are also accomplished by a method for the production of a medical tool manifesting lubricity on being wetted, which method comprises coating the surface of a matric material having as a component thereof a synthetic polymeric compound containing an acid anhydride group in the molecular unit thereof with a water-swellable polymer possessed of a functional group capable of reacting with the acid anhydride group and subsequently heat-treating the coated matric material at a temperature of not lower than 40° C.

The objects described above are further accomplished by a method for the production of a medical tool manifesting lubricity on being wetted, which method comprises coating the surface of a matric material having as a component thereof a synthetic polymeric compound containing an acid anhydride group in the molecular unit thereof with a water-swellable polymer possessed of a functional group capable of reacting with the acid anhydride group and subsequently cross-linking the water-swellable polymer.

This invention discloses a medical tool forming a lubricious surface on being wetted, wherein a water-swellable polymer containing in the molecular unit thereof at least one reactive functional group selected from among epoxy group, acid halide group, and isocyanate group is applied in the form of a coating to the surface of a matric material containing a proton-donating group such as amino group, imino group, hydroxyl group, carboxyl group, or mercapto group which is capable of reacting with the reactive functional group mentioned above. This invention also discloses a medical tool, wherein a water-swellable polymer containing in the molecular unit thereof at least one reactive functional group such as hydroxyl group, amino group, or epoxy group which is capable of reacting with an acid anhydride is applied in the form of a coating to the surface of a matric material containing an acid anhydride group in the molecular unit thereof. This invention further discloses a medical tool, wherein a water-swellable polymer is introduced fast chemically in the surface of the matric material. For the reason above, the medical tool of this invention can retain high safety intact because it never entails such phenomenon of an applied coat exfoliating, peeling, or melting from the surface of a matric material as is observed in the case of a method which involves application of silicone oil, olive oil, or glycerol to the surface of a matric material.

Further, in the medical tool of this invention, the surface of the matric material thereof offers extremely low friction resistance particularly when it is in a state wet with such bodily humor as saliva, digestive fluid, or blood or such aqueous liquid as physiological saline solution or water. When the catheter, i.e. one form of the medical tool of this invention, is inserted in a patient's body, therefore, it is at an advantage in facilitating the insertion, alleviating the patient's pain, and precluding infliction of injury to the mucous membrane or the inner wall surface of blood vessel, for example.

Besides, since this invention does not need to use such a highly reactive cross-linking compound as diisocyanate for the sake of the coating work but permits impartation of ample prospective lubricity on the surface of the matric material by just one coating work, the medical tool of this invention excels in operability and safety and imposes virtually no restriction on the matric material. Thus, this invention can be embodied in a promiscuous collection of medical tools.

EXPLANATION OF THE PREFERRED EMBODIMENT

Figure 1:
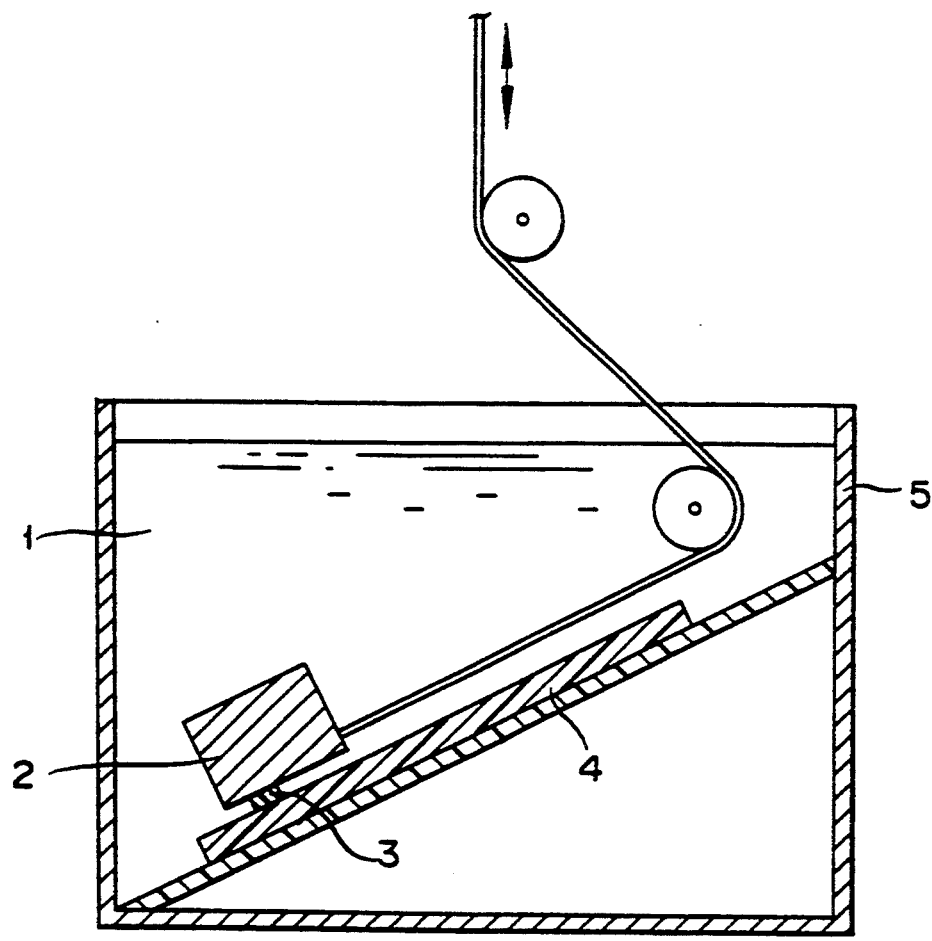
FIG. 1 is a schematic diagram illustrating a method of testing for lubricity and FIG. 2 is a schematic diagram illustrating a catheter as one preferred embodiment of the medical tool of this invention.

In this invention, the water-swellable polymer which manifests lubricity in a wet state is only required to be capable of manifesting this lubricity on contact with body fluid or aqueous solvent. With respect to the ease with which the polymer is synthesized and the convenience with which the polymer is worked, acrylamide, acrylamide derivatives such as dimethyl acrylamide, maleic anhydride, vinyl methyl ether, etc. may be cited as preferable polymers which answer the description given above. The polymer under discussion is preferable to use dimethyl acrylamide as a main component thereof. A copolymer (I) which comprises a moiety destined to manifest lubricity and a moiety incorporating the aforementioned reactive functional group therein proves particularly preferable. The moiety manifesting lubricity is required to account for a proportion of not less than 40 parts by weight, preferably not less than 60 parts by weight, and more preferably not less than 80 parts by weight, in the total amount of the water-swellable polymer. The moiety incorporating the reactive functional group is required to account for a proportion of not less than 1 part by weight, preferably not less than 10 parts by weight, and more preferably not less than 20 parts by weight. Produced by synthesis, the polymer capable of manifesting lubricity on contact with liquid may be chemically treated to be partially substituted by an epoxy group, an acid halide group, an isocyanate group, etc.

Further, the matric material of the medical tool aimed at by this invention may be a shaped article formed chiefly of such a material as modified polyolefin, polyether, polyurethane, polyamide, polyimide, or nylon, which is a substance containing a functional group capable of reacting with the epoxy group, acid halide group, isocyanate group, etc., namely a proton-donating group such as amino group, imino group, hydroxyl group, carboxyl group, or mercapto group or a multilayer shaped article using other material in addition to the material mentioned above or a shaped article of an alloy based on the same material as mentioned above. In the light of the convenience of handling, it is preferable to use a polyolefin modified with acrylic acid for the matric material. At least part of the surface of the matric material of the medical tool, when necessary, may be treated as by the method of plasma-initiated graft polymerization so as to introduce a proton-donating group therein. The content of the material in the medical tool, though variable with the mechanical strength and other qualities to be preferable, is at least 50 parts by weight, preferably at least 70 parts by weight, and more preferably at least 90 parts by weight.

The term "acid anhydride" refers to a compound which is formed by the condensation of two molecules of carboxylic acid with loss of one molecule of water and is represented by the general formula, $(RCO)_2O$. Though the synthetic polymeric compound which contains an acid anhydride group in the molecular unit thereof is not particularly limited, monomers containing an acid anhydride group such as, for example, polymeric compounds synthetically formed by copolymerizing maleic anhydride may be cited as preferred examples. Polyethylenes and polypropylenes which contain maleic anhydride are particularly preferable examples. The demand for the polyolefins containing maleic anhydride as an adhesive polymer fit for the modification of an olefin or the lamination of a multilayer olefin product has been growing in recent years. They are produced and marketed under a general designation of "Modified Polyolefins" and, therefore, are readily available. They are thermoplastic polymers excelling in formability and prove preferable in terms of physical properties, workability, stability (resistance to aging), safety, and cost.

The synthetic polymeric compound containing an acid anhydride has only to be present in the surface layer of the matric material. The matric material, therefore, may be what is manufactured by forming the polymeric compound as a simple substance in a prescribed shape or what is manufactured by having an alloy of the polymeric compound deposited on the surface of a matric material formed preparatorily in the prescribed shape. For example, a layer of the synthetic polymeric compound containing an acid anhydride group may be deposited by the multilayer molding, laminating, coating, or blending technique only on such a portion of the surface of a matric material of polyolefin, polyether, polyurethane, polyamide, polyimide, polyester, or copolymer thereof as is required to offer low friction.

The content of the acid anhydride group is preferable to exceed 0.01 mol %, preferably to fall in the range of 0.5 to 50 mol %, based on the amount of the molar composition of the monomer forming the synthetic polymeric compound plus the acid anhydride group. The functional groups which effectively react with the acid anhydride group include hydroxy group, amino group, and epoxy group, for example. From the viewpoint of reactivity, the epoxy group proves preferable among other functional groups mentioned above. The water-swellable polymer containing such a functional group is a polymeric compound which is dissolved or swelled with water. As typical examples of the water-swellable polymer, copolymers (II) of such hydrophilic monomers as acryl amides including acryl amide and dimethyl acrylamide, vinyl pyrrolidone, and vinyl ethers with monomers containing such a functional group as mentioned above may be cited. In the water-swellable polymer, the content of the functional group capable of reacting with the acid anhydride group is preferable to be in the range of 2 to 50%, preferably 5 to 25%, based on the molar composition of the hydrophilic monomer and the acid anhydride group.

As a method for binding the copolymer (II) to the surface of the matric material, a heat treatment to be carried out at a temperature exceeding 30° C. is available. The heat treatment promotes the reaction of the water-swellable polymer with the acid anhydride on the surface of the matric material and the reaction of the water-swellable polymer. The temperature of this heat treatment is preferable to be in the range of 30° to 120° C., preferably 50° to 80° C. For the purpose of promoting the reaction of the acid anhydride, a catalyst, particularly the catalyst using such a tertiary amine compound as a trialkyl amine compound or pyridine, is used advantageously. Then, for the purpose of improving the durability or controlling the lubricity of the hydrophilic low-friction surface, the water-swellable polymer may be coated and then subjected to a cross-linking treatment. To be specific, the strength of the lubricious surface layer can be exalted without appreciably decreasing the lubricity thereof by allowing a three-dimensional reticular structure to be formed in a small amount within the surface layer. If the cross-linked structure is unduly large, however, the ability of the surface layer to swell with absorbed liquid is lowered and the ability of the surface to resist friction is impaired. Thus, the formation of a cross-link in the surface layer calls for due advertence. The cross-linkage may be attained by any of the various conventional methods widely known in the art. The polymer may be cross-linked, for example, by generating an active radical by means of light, heat, or radiation. Besides, a method which involves addition of a polymerizing polyfunctional monomer, a method which involves application of a polyfunctional cross-linking agent, and a method which resorts to cross-linkage of functional groups in the molecular unit through the medium of a catalyst may be cited as typical examples of the conventional methods mentioned above. In the case of a water-swellable polymer containing such a highly reactive functional group as an epoxy group, for example, the polymer between epoxy groups can be easily cross-linked with a diamino compound, dihydroxy compound, dialdehyde compound, etc.

The copolymers (I) or copolymers (II) may occur as random, block, and graft copolymers. The block or graft copolymers prove preferable. The preference of the block copolymers and the graft copolymers over the random copolymers will be demonstrated below with reference to copolymers of vinyl pyrrolidone (VP) and glycidyl methacrylate (GMA). The block copolymers and the graft copolymers severally of VP and GMA possess a domain manifesting reactivity (poly GMA) and exhibit strong reactivity and bonding property with the acid anhydride group on the surface of the matric material as compared with polymers which have reactive groups (GMA) and hydrophilic groups (VP) randomly dispersed therein. This fact may be logically explained by a postulate that the poly GMA part is hydrophobic as compared with the poly VP part and excels the poly VP part in adhesiveness to the surface of the matric material and, therefore, gains in reactivity with the acid anhydride group in the surface layer of the matric material. As respects the union (cross-linkage) of molecules through the medium of the poly GMA domain, the surface layer is so modified as to acquire increased strength because a plurality of bonds (cross-links) are formed after the pattern of a chain. The randomly introduced GMA, by contrast, possesses less reactivity with the acid anhydride on the surface of the matric material owing to the influence of the VP which exists in proximity of the GMA molecules. Further, the poly DMAA domains such as are contained in the block copolymers have an ample capacity for absorbing water and, therefore, are enabled to manifest ideal lubricity. The copolymers which have GMA randomly dispersed therein suffer from poor lubricity because the ability of DMAA to absorb water or swell with water is restrained by the intramolecular cross-linkage randomly formed between GMA's and the hydrophobicity of the GMA itself.

The term "medical tool" as used in this invention refers to a medical tool which has formed on either the inner side or the outer side thereof a surface required to offer low resistance to friction during the insertion, slide, or retention of the medical tool in a patient's body when the surface is wetted with such a bodily fluid as saliva, digestive fluid, or blood or an aqueous liquid such as physiological saline solution or water. Thus, the following items may be cited as typical examples of the medical tool of this invention.

1) Catheters such as stomach catheter, feeding tube, and ED tube which are inserted via the mouth or nose into the stomach and at times left indwelling therein.

2) Tubes or cuffs of oxygen catheters, oxygen cannulas, and windpipes, tubes and cuffs of tracheotomy tubes, and catheters such as intratracheal aspiration catheters which are inserted via the mouth or nose into the windpipe and at times left indwelling therein.

3) Catheters such as catheters and balloons in urethral catheters, urinal catheters, and balloon catheters which are inserted into the urethra or the renal duct and at times left indwelling therein.

4) Catheters such as suction catheters, fluid discharge catheters, and rectal catheters which are inserted into various body cavities or tissues and at times left indwelling therein.

5) Catheters such as indwelling needles, IVH catheters, thermodalution catheters, angiographic catheters, vasodilating catheters, dilators, or introducers which are inserted into or left indwelling in the blood vessel and guide wires and stylets for such catheters.

6) Endoscopes, contact lenses, etc. for insertion into various internal organs.

Now, this invention will be described more specifically below with reference to working examples of the invention.

EXAMPLES 1 to 3

(A) Production of block copolymer

To 72.3 g of adipic acid dichloride, 29.7 g of triethylene glycol was added dropwise at 50° C. The resultant mixture was subjected to reduced-pressure distillation at 50° C. for 3 hours to expel the consequently separated hydrochloric acid and obtain 22.5 g of oligoester. The oligoester in this amount and 4.5 g of methylethyl ketone added thereto were together added dropwise into a solution comprising 5 g of sodium hydroxide, 6.93 g of 31% hydrogen peroxide, 0.44 g of a surfactant of dioctyl phosphate, and 120 g of water and left reacting therein at −5° C. for 20 minutes. The product consequently obtained was washed with water, washed repeatedly with methanol, and then dried to obtain a polyperoxide (PPO) containing a plurality of peroxide groups in the molecular unit thereof. With 0.5 g of this PPO as a polymerization initiator, 9.5 g of glycidyl methacrylate (GMA) placed in 30 g of benzene as a solvent was stirred at 65° C. for 24 hours under a reduced pressure to be polymerized. The reaction product was reprecipitated in diethyl ether to obtain polyglycidyl methacrylate (PGMA) containing a peroxide group in the PGMA molecular unit. Then, 1.0 g of the PGMA, 9.0 g of dimethyl acryl amide, and 90 g of dimethyl sulfoxide as a solvent were combined, sealed in a reaction vessel under a reduced pressure, and heated at 80° C. for 18 hours to polymerize the monomer. The resultant reaction solution was poured into 2 liters of rapidly stirred diethyl ether to effect separation of a precipitate. The precipitate was isolated by filtration. The separated precipitate was repeatedly refined with tetrahydrofuran (THF) as a good solvent and diethyl ether as a poor solvent and then subjected to reduced-pressure distillation to obtain a block copolymer.

The procedure described thus far was repeated excepting methacrylic acid chloride was used in Example 2 and methacryloyl-oxyethyl isocyanate was used in Example 3 respectively instead of the GMA mentioned above.

(B) Method of test for lubricity

A modified polyolefin (polyethylene modified with methacrylic acid) sheet (produced by Mitsui-DuPont K.K. and marketed under trademark designation of "Nuclei N-1525") was kept immersed in a THF solution containing the aforementioned block polymer in a concentration of 2% by weight at normal room temperature for 30 seconds and then heat-treated for reaction in an oven at 80° C. for 18 hours. Consequently, a lubricious sheet material was obtained.

In a body of water 1 held in a water tank 5, a cylindrical iron weigh 2 having a weight of 1 kg was gently mounted on a sheet 4 attached fast to a plastic plate 6 inclined at an angle of 30° with the aid of the lubricious sheet 3 as illustrated in FIG. 1. The weigh 2 was slid repeatedly 100 times at a speed of 100 mm/min. on the sheet 4 over a width of 1 cm to determine the value of resistance to the friction due to the slide.

The value of resistance to the final friction after the 100th slide of the weigh on the inclined sheet as the index of lubricity and the change in the value of resistance to friction (Δ value of resistance to friction) of the following formula (1) as the index of continuous lubricity are shown in Table 1.

Δ Value of resistance to friction=(Value of resistance to final friction)−(Value of resistance to initial friction) (1)

Control 1

The same sheets as obtained in Examples 1 to 3 in their uncoated state were tested for lubricity in the same manner as in Example 1. The results are shown in Table 1.

EXAMPLES 4 to 6

(A) Production of random copolymer

A reaction vessel sealable by fusion was charged with 1.0 g of a varying compound (monomer) indicated in Table 1, 9.0 g of dimethyl acryl amide, 0.05 g of azo-bis-isobutyronitrile as an initiator, and 90 g of dimethyl sulfoxide, sealed by fusion under a reduced pressure, and then heated to 80° C. for 18 hours to induce polymerization of the monomers. The reaction solutions were refined in the same manner as in Examples 1 to 3.

(B) Method of test for lubricity

The surface of a polypropylene sheet (produced by Futamura Kagaku K.K. and marketed under product code of "FOP #60") was irradiated for 10 seconds with a low-temperature plasma (Ar: 0.1 Torr) and supplied with methacrylic acid monomer in the gase phase and simultaneously heated at a temperature of 288 K. to graft the surface. The sheet was washed for one day with a good solvent for polymethacrylic acid and then dried. The dry sheet was kept immersed in a THF solution containing the random copolymer in a concentration of 2% by weight at normal room temperature for 30 seconds and then heat-treated to induce a reaction in an oven at 80° C. for 18 hours. Consequently, a lubricious sheet was obtained. The test for lubricity was carried out in the same manner as in Examples 1 to 3. The results are shown in Table 1.

Control 2

The same sheets as treated in Examples 4 to 6 in their uncoated state were tested for lubricity. The results are shown in Table 1.

EXAMPLE 7

(A) Production of random copolymer

A reaction vessel sealable by fusion was charged with 2.0 g of glycidyl acrylate, 8.0 g of maleic anhydride, 0.05 g of azo-bis-isobutyronitrile as an initiator, and 90 g of dimethyl sulfoxide as a solvent, sealed by fusion under a reduced pressure, and then heated at 80° C. for 18 hours to polymerize the monomers. The produced copolymer was refined in the same manner as in Examples 1 to 3.

(B) Method of test for lubricity

A polyurethane sheet (produced by Dow Chemical Company and marketed under trademark designation of "Pellethane") was kept immersed in a THF solution containing the random polymer at a concentration of 2% by weight at normal room temperature for 30 seconds and then heated to induce a reaction in an oven at 80° C. for 18 hours. Then, the maleic anhydride portion of the polymer deposited fast on the sheet was heated in ethanol with sulfuric acid as a catalyst at 60° C. for 6 hours to open the ring and form a half ester of ethanol. Finally, this sheet was given an alkali washing in an aqueous 0.1% by weight of sodium chloride solution containing NaHCO$_3$ at a concentration of 0.01% by weight at 60° C. for 18 hours. Consequently, a lubricious sheet was obtained. The sheet was tested for lubricity in the same manner as in Examples 1 to 3. The results are shown in Table 1.

Control 3

The same sheet as produced in Example 7 in its uncoated state was tested for lubricity. The results are shown in Table 1.

(B) Method of test for lubricity

Figure 2:
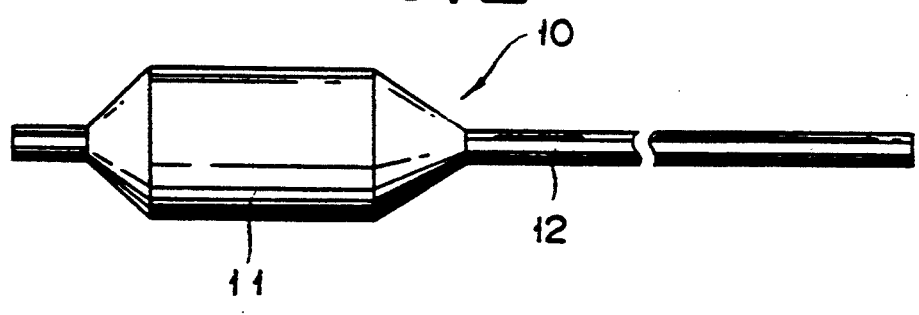

The surface of a balloon 11 (3 mm in outside diameter and 45 mm in length) of polyethylene terephthalate illustrated in FIG. 2 was irradiated with a low-temperature plasma (Ar: 0.1 Torr) for 10 seconds and then supplied with methacrylic acid monomer in the gaseous phase and simultaneously heated at a temperature of 288 K. to graft the surface. The balloon 11 was washed with good solvent for polymethacrylic acid for one day and dried. The dried balloon 11 was treated in the same manner as in Example 8 to obtain a lubricious balloon 11. The balloon 11 was connected to a tube 12 (1 mm in outside diameter) to form a catheter 10. This catheter 10 was tested for lubricity by touch of a finger. The results are shown in Table 1.

TABLE 1

| Sample No. | Matric material | Copolymer Monomer 1 | Monomer 2 | Value of resistance to final friction | Δ value of resistance to friction |
| --- | --- | --- | --- | --- | --- |
| Example 1 | Modified polyolefin | Glycidyl methacrylate | Dimethyl acrylamide | 62 gf | 0 |
| Example 2 | Modified polyolefin | Methacrylic acid chloride | Dimethyl acrylamide | 67 gf | 0 |
| Example 3 | Modified polyolefin | Methacryloyloxy ethyl isocyanate | Dimethyl acrylamide | 64 gf | 0 |
| Example 4 | PP-g-MAA | Glycidyl methacrylate | Dimethyl acrylamide | 77 gf | 0 |
| Example 5 | " | Methacrylic acid chloride | Dimethyl acrylamide | 73 gf | 0 |
| Example 6 | " | Methacryloyloxy ethyl isocyanate | Dimethyl acrylamide | 72 gf | 0 |
| Example 7 | Polyurethane | Glycidyl acrylate | Maleic anhydride | 87 gf | 0 |
| Example 8 | PET-g-MAA | Glycidyl acrylate | Maleic anhydride | 83 gf | 0 |
| Example 9 | " | Glycidyl acrylate | Maleic anhydride | Excellent | Excellent |
| Control 1 | Modified polyolefin | — | — | 431 gf | 234 gf |
| Control 2 | PP-g-MAA | — | — | 386 gf | 82 gf |
| Control 3 | Polyurethane | — | — | 412 gf | 186 gf |
| Control 4 | PET-g-MAA | — | — | 377 gf | 84 gf |

EXAMPLE 8

(A) Production of random copolymer

The procedure of Example 7 was faithfully repeated for polymerization and refinement.

(B) Method of test for lubricity

The surface of a polyethylene terephthalate sheet (produced by Dia Foil K.K. and marketed under product code of "H100") was irradiated with a low-temperature plasma (Ar: 0.1 Torr) for 10 seconds and then supplied with methacrylic acid monomer in the gaseous phase and simultaneously heated at a temperature of 288 K. to be grafted. The sheet was washed with a good solvent for polymethacrylic acid for one day and dried. The dried sheet was treated in the same manner as in Example 7 to obtain a lubricious sheet. The test for lubricity was carried out in the same manner as in Examples 1 to 3. The results are shown in Table 1.

Control 4

The same sheet as produced in Example 8 in its uncoated state was tested for lubricity. The results are shown in Table 1.

EXAMPLE 9

(A) Production of random copolymer

The procedure of Example 8 was faithfully repeated for both polymerization and refinement. The results are shown in Table 1.

Note)
(PP-g-MAA: Graft polymerization of methacrylic acid monomer to polypropylene
PET-g-MAA: Graft polymerization of methacrylic acid monomer to polyethylene terephthalate

EXAMPLES 10 and 11

A block copolymer of Example 10 was obtained by polymerizing 3.0 g of polyglycidyl methacrylate and 12.5 g of dimethyl acrylamide by following the procedure described in (A) production of block copolymer in Example 1.

A random copolymer of Example 11 was obtained by polymerizing 3.0 g of glycidyl methacrylate and 12.5 g of dimethyl acrylamide by following the procedure described in (A) production of random copolymer in Example 4.

Tetrahydrofuran solutions severally containing the block copolymer and the random copolymer mentioned above at a fixed concentration of 2% by weight were tested for lubricity in the same manner as in Examples 1 to 3, but slide time was 500. The results are shown in Table 2.

TABLE 2

| Kind of polymer | DMAA : GMA (found by NMR) | Value of resistance (gf) Initial | Δ value |
|---|---|---|---|
| Block copolymer of Example 10 | 7.81 : 1 | 89.2 | 2.6 |
| Random copolymer of Example 11 | 7.78 : 1 | 75.8 | 37.5 |

EXAMPLES 12 to 14

A block copolymer (Example 12) having poly GMA as a reactive domain and poly DMAA as a hydrophilic domain was obtained by placing 8 g of dimethyl acrylamide (DMAA) as a hydrophilic monomer in DMSO using 1 g of the poly GMA of Example 1 as a polymerization initiator and polymerizing the monomers at 70° C. for 18 hours. On analysis by NMR, the resultant copolymer was found to be composed of DMAA and GMA at a ratio of 10.1:1. In the same manner as described above, a block copolymer composed of DMAA and GMA at a ratio of 7.1:1 was obtained in Example 13 and a block copolymer composed of vinyl pyrrolidone and GMA at a ratio of 6.6:1 in Example 14.

A sheet (200 μm of an ethylene-acrylic ester-maleic anhydride terpolymer (produced by Sumika-CDF Kagaku K.K. and marketed under trademark designation of "Bondine TX8030") was kept immersed in a tetrahydrofuran (THF) solution (containing 1% by weight of pyridine) containing the block copolymer at a concentration of 2% at 25° C. for 30 seconds, heat-treated for reaction in an oven at 80° C. for 18 hours, washed with water, and dried. The produced sheet, on exposure to moisture, assumed a ropy lubricious surface offering only low resistance to friction.

When the block copolymers were tested for lubricity with an apparatus shown in FIG. 1 in the same manner as in Examples 1 to 8, the values of resistance to friction were in the neighborhood of 70 gf and the values of Δ resistance to friction were invariably below 10 gf. In the test of 100 slides on the plate, they showed low friction resistance stably. When the obverse surface and the cross section of each of the sheets were visually examined under a scanning type electron microscope (produced by Japan Electron Optics Laboratory Co., Ltd. and marketed under product code of "JSM 840"), no change was found before and after the test. This fact indicates that the modified surface layers were bound so fast to the sheets as to defy separation.

Control 5

The same matric sheets (ethylene-acrylic ester-maleic anhydride terpolymer) 200 μm in thickness as used in Examples 12 to 14 were tested in the same manner as in Examples 12 to 14. The results are shown in Table 3.

The values of Δ resistance to friction were larger presumably because the oxide layers in the uppermost surface parts of the sheets were scraped by friction between adjoining surfaces.

EXAMPLE 15

A block copolymer composed of DMAA and GMA at a ratio of 2.8:1 was synthesized by following the procedure of Example 12. This block copolymer was deposited fast on a sheet (200μ of an ethylene-acrylic ester-maleic anhydride terpolymer (produced by Sumika CDF Kagaku K.K. and marketed under trademark designation of "Bondine TX8030") in the same manner as in Examples 12 to 14 and was tested in the same manner as in Examples 12 to 14. The results are shown in Table 3.

EXAMPLE 16

An ethylene-acrylic ester-maleic anhydride terpolymer (produced by Sumika-CDF Kagaku K.K. and marketed under trademark designation of "Bondine TX8030") and polyethylene were blended at a ratio of 1:1 and the resultant blend was manufactured into a catheter tube measuring 3 mm in inside diameter and 4 mm in outside diameter. The same THF 2% block copolymer solution (containing 1% by weight of pyridine) as used in Example 12 was injected into the tube by the use of a syringe pump, left standing in the tube at normal room temperature for 30 seconds, and discharged from the tube. Then, the tube was treated in an oven at 80° C. for 18 hours, washed with water, dried, and cut open with a knife to expose the interior surface thereof, left to be hit by dripping water, and tested for lubricity. It was found to have formed a ropy surface offering only low resistance to friction.

EXAMPLE 17

An X-ray contrast catheter (3.6 mm in outside diameter) was produced with a blend of an ethylene-acrylic ester-maleic anhydride terpolymer (produced by Sumika-CDF Kagaku K.K. and marketed under trademark designation of "Bondine AX8390") with 50% by weight of tungsten as a sensitizer. This tube was left immersed in a THF solution (containing 1% by weight of pyridine) containing the block copolymer of Example 13 at a concentration of 2% at normal room temperature for three seconds, dried, and heated for reaction in an oven at 60° C. for 40 hours. The tube was then washed with water, dried, and then left to be hit by dripping water to determine lubricity. It was consequently found to have formed a ropy surface offering only low resistance to friction. After it had been forcibly rubbed 20 times with a finger tip, it still retained lubricity intact.

EXAMPLE 18

A catheter 3 mm in inside diameter and 4 mm in outside diameter was produced with a material obtained by blending an ethylene-acrylic ester-maleic anhydride terpolymer (produced by Sumika-CDF Kagaku K.K. and marketed under trademark designation of "Bondine TX8030") and polyethylene at a ratio of 1:1. This tube was kept immersed in a solution of THF (containing 1% by weight of triethyl amine) containing the block polymer of Example 12 at a concentration of 2% by weight and further containing 0.1% of hexamethylene diamine as a cross-linking agent at normal room temperature for 30 seconds and then heated for reaction in an oven at 80° C. for 18 hours. When this tube was immersed in a physiological saline solution and rubbed with a finger tip, it was found to have formed a low-friction surface highly slippery as compared with an untreated tube.

TABLE 3

| | Value of resistance to final friction | Δ value of resistance to friction |
|---|---|---|
| Example 12 | 62 gf | 10 gf max. |
| Example 13 | 72 gf | 10 gf max. |
| Example 14 | 70 gf | 10 gf max. |
| Control 5 | 443 gf | 72 gf |
| Example 15 | 172 gf | 10 gf max. |

What is claimed is:

1. A medical tool comprising:
   a water-swellable polymer comprising a moiety manifesting lubricity and another moiety having a first reactive functional group selected from the group consisting of an epoxy group, an acid halide group, and an isocyanate group in the molecular unit thereof; and
   a material, chemically bonded to said water-swellable polymer by means of a proton-donating group of said material, capable of reacting with said first reactive functional group, said proton-donating group selected from the group consisting of an amino group, an imino group, a hydroxy group, a carboxyl group, a mercapto group, or mixtures thereof;
   said medical tool exhibiting lubricity in a wetted state.

2. The medical tool according to claim 1, wherein said first moiety is derived from at least one hydrophilic monomer selected from the group consisting of di-methyl acrylamide and maleic anhydride.

3. The medical tool according to claim 1, wherein said second moiety is derived from at least one monomer selected from the group consisting of glycidyl methacrylate, methacrylic acid chloride, methacryloyloxy ethyl isocyanate, and glycidyl acrylate.

4. The medical tool according to claim 1, wherein said water-swellable polymer contains at least one co-polymer selected from the group consisting of a block copolymer and a graft copolymer.

5. The medical tool according to claim 4, wherein said copolymer is a block copolymer.

6. The medical tool according to claim 5, wherein said block copolymer comprises glycidyl methacrylate and dimethyl acrylamide.

7. The medical tool according to claim 1, wherein said material is at least one member selected from the group consisting of a modified polyolefin, polyether, polyurethane, polyamide, polyimide and nylon.

8. The medical tool according to claim 7, wherein said modified polyolefin is a polyolefin modified with methacrylic acid.

9. The medical tool according to claim 1, wherein said proton-donating group is a carboxyl group.

10. A medical tool according to claim 1, which is a catheter.

11. A medical tool comprising:
    a water-swellable polymer comprising a moiety manifesting lubricity and another moiety having a reactive functional group selected from the group consisting of a hydroxy group, an amino group, and an epoxy group in the molecular unit thereof; and
    a material chemically bonded to said water-swellable polymer by means of an acid anhydride group of said material capable of reacting with said reactive functional group;
    said medical tool exhibiting lubricity in a wetted state.

12. The medical tool according to claim 11, wherein said moiety manifesting lubricity is derived from at least one hydrophilic monomer selected from the group consisting of dimethyl acrylamide, acrylamide, vinyl pyrrolidone, and vinyl ether.

13. The medical tool according to claim 11, wherein said another moiety is derived from glycidyl methacrylate.

14. The medical tool according to claim 11, wherein said water-swellable polymer contains at least one co-polymer selected from the group consisting of a block copolymer and a graft copolymer.

15. The medical tool according to claim 14, wherein said copolymer is a block copolymer.

16. The medical tool according to claim 15, wherein said block copolymer comprises glycidyl methacrylate and dimethyl acrylamide.

17. The medical tool according to claim 11, wherein said acid anhydride is maleic anhydride.

18. The medical tool according to claim 11, which is a catheter.

* * * * *